(12) United States Patent
Pinkos et al.

(10) Patent No.: US 8,629,306 B2
(45) Date of Patent: Jan. 14, 2014

(54) METHOD FOR PRODUCING 1,6-HEXANEDIOL

(75) Inventors: Rolf Pinkos, Bad Duerkheim (DE); Daniel Breuninger, Bobenheim-Roxheim (DE); Gerd-Dieter Tebben, Mannheim (DE)

(73) Assignee: BASF SE, Ludwigshafen (DE)

( * ) Notice: Subject to any disclaimer, the term of this patent is extended or adjusted under 35 U.S.C. 154(b) by 296 days.

(21) Appl. No.: 13/257,496

(22) PCT Filed: Mar. 29, 2010

(86) PCT No.: PCT/EP2010/054053
§ 371 (c)(1),
(2), (4) Date: Sep. 19, 2011

(87) PCT Pub. No.: WO2010/115738
PCT Pub. Date: Oct. 14, 2010

(65) Prior Publication Data
US 2012/0022298 A1 Jan. 26, 2012

(30) Foreign Application Priority Data
Apr. 7, 2009 (EP) ...................................... 09157511

(51) Int. Cl.
*C07C 27/04* (2006.01)

(52) U.S. Cl.
USPC ........... 568/884; 568/864; 568/868; 568/903; 568/910; 568/913

(58) Field of Classification Search
None
See application file for complete search history.

(56) References Cited

U.S. PATENT DOCUMENTS

| 3,933,930 | A | 1/1976 | Dougherty et al. | |
|---|---|---|---|---|
| 8,471,042 | B2 * | 6/2013 | Pinkos et al. | 549/266 |
| 2007/0112225 | A1 | 5/2007 | Sirch et al. | |
| 2008/0207958 | A1 | 8/2008 | Haunert et al. | |
| 2010/0168445 | A1 * | 7/2010 | Pinkos et al. | 549/266 |
| 2010/0240913 | A1 | 9/2010 | Pinkos et al. | |
| 2010/0256398 | A1 | 10/2010 | Pinkos et al. | |
| 2011/0015429 | A1 | 1/2011 | Pinkos et al. | |
| 2011/0124905 | A1 | 5/2011 | Pinkos et al. | |
| 2011/0124926 | A1 | 5/2011 | Pinkos et al. | |

FOREIGN PATENT DOCUMENTS

| DE | 1 235 879 | 3/1967 |
|---|---|---|
| DE | 2 060 548 | 6/1972 |
| DE | 2 321 101 | 11/1974 |
| DE | 196 07 954 | 9/1997 |
| DE | 197 38 464 | 3/1999 |
| DE | 103 13 702 | 10/2004 |
| DE | 10 2004 054 047 | 5/2006 |
| EP | 0 552 463 | 7/1993 |
| WO | 99 03801 | 1/1999 |
| WO | 2006 005504 | 1/2006 |
| WO | 2008 152001 | 12/2008 |

OTHER PUBLICATIONS

"Ullmann's Encyclopedia of Industrial Chemistry, Fifth, Completely Revised Edition," VCH, vol. A8: Coronary Therapeutics to Display Technology, pp. 217-227, (1987).
Houben-Weyl, H. K., "Methods of Organic Chemistry," Georg Thieme Verlag Stuttgart, vol. IV/1c, pp. 16-29, (1980).
Houben-Weyl, H. K., "Methods of Organic Chemistry," Georg Thieme Verlag Stuttgart, vol. IV/1c, pp. 44-67, (1980).
International Search Report Issued Sep. 16, 2010 in PCT/EP10/054053 Filed Mar. 29, 2010.
U.S. Appl. No. 13/133,006, filed Jun. 6, 2011, Abillard, et al.
U.S. Appl. No. 13/258,166, filed Sep. 21, 2011, Pinkos, et al.
U.S. Appl. No. 13/226,049, filed Sep. 6, 2011, Abillard, et al.
U.S. Appl. No. 13/258,207, filed Sep. 21, 2011, Abillard, et al.
U.S. Appl. No. 13/381,116, filed Dec. 28, 2011, Kunst, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to a process for preparing 1,6-hexanediol, preferably with at least 99.5% purity, which are especially virtually free of 1,4-cyclohexanediols, from a carboxylic acid mixture which is obtained as a by-product of the catalytic oxidation of cyclohexane to cyclohexanone/cyclohexanol with oxygen or oxygen-comprising gases and by water extraction of the reaction mixture, by hydrogenating the carboxylic acid mixture, esterifying and hydrogenating a substream to hexanediol.

20 Claims, 2 Drawing Sheets

METHOD FOR PRODUCING 1,6-HEXANEDIOL

The invention relates to a process for preparing 1,6-hexanediol, preferably with at least 99.5% purity, which are especially virtually free of 1,4-cyclohexanediols, from a carboxylic acid mixture which is obtained as a by-product of the catalytic oxidation of cyclohexane to cyclohexanone/cyclohexanol with oxygen or oxygen-comprising gases and by water extraction of the reaction mixture, by hydrogenating the carboxylic acid mixture, esterifying and hydrogenating a substream to hexanediol.

1,6-Hexanediol is a sought-after monomer unit which is used predominantly in the polyester and polyurethane sectors.

The aqueous solutions of carboxylic acids which arise as by-products in the catalytic oxidation of cyclohexane to cyclohexanol and cyclohexanone (cf. *Ullmann's Encyclopedia of Industrial Chemistry*, 5th Ed., 1987, Vol. A8, p. 219), referred to hereinafter as dicarboxylic acid solution (DCS), comprise (calculated without water in % by weight) generally between 10 and 40% adipic acid, between 10 and 40% 6-hydroxycaproic acid, between 1 and 10% glutaric acid, between 1 and 10% 5-hydroxyvaleric acid, between 1 and 5% 1,2-cyclohexanediols, between 1 and 5% 1,4-cyclohexanediols, between 2 and 10% formic acid, between 0.5 and 5% 4-hydroxycyclohexanone, between 0.5 and 10% 6-oxocaproic acid and a multitude of further mono- and dicarboxylic acids, esters, oxo and oxa compounds, the individual contents of which generally do not exceed 5%. Examples include acetic acid, propionic acid, butyric acid, valeric acid, caproic acid, oxalic acid, malonic acid, succinic acid, 4-hydroxybutyric acid and 2- or 3-hydroxyadipic acid.

DE 2 321 101 and DE 1 235 879 disclose hydrogenating these aqueous dicarboxylic acid solutions at temperatures of 120 to 300° C. and pressures of 50 to 700 bar in the presence of predominantly cobalt-comprising catalysts to give 1,6-hexanediol as the main product. The hydrogenation outputs are preferably worked up by distillation. Even with an extremely high level of distillation complexity, it is possible to remove the 1,4-cyclohexanediols unchanged in the hydrogenation from 1,6-hexanediol only incompletely, if at all, such that the 1,4-cyclohexanediols which were already present initially in the DCS are found again in the 1,6-hexanediol with a content of generally 2 to 5% by weight.

In order to counter this problem, some approaches to solutions are known: U.S. Pat. No. 3,933,930 describes the conversion of 1,4-cyclohexandiol in aqueous solutions of adipic acid and 6-hydroxycaproic acid to cyclohexanol, cyclohexane and/or cyclohexene, by catalytically prehydrogenating the mixture. This process requires the use of two different hydrogenation catalysts, one for the prehydrogenation and one for the actual carboxylic acid hydrogenation, and is therefore costly and inconvenient.

According to DE-A 2 060 548, very pure 1,6-hexanediol is obtained by crystallization. This process too is very costly and inconvenient, and is also associated with considerable yield losses.

A further means of obtaining high-purity 1,6-hexanediol consists in hydrogenating, instead of DCS, pure adipic acid or pure adipic ester, as described by K. Weissermel, H. J. Arpe in Industrielle Organische Chemie [Industrial Organic Chemisry], VCH-Verlagsgemeinschaft Weinheim, 4th edition, page 263, 1994. However, pure adipic acid is very expensive compared to DCS. Furthermore, the carboxylic acid mixture obtained in the cyclohexane oxidation is a waste product which should be sent to a material utilization for environmental reasons among others. Caprolactone also cannot be obtained from adipic acid in a simple manner.

DE-A 196 07 954 already describes a process which describes obtaining 1,6-hexanediol from abovementioned aqueous carboxylic acid mixtures. This process, which is elegant in itself, however, still has certain disadvantages. For instance, not all linear C6 components present in the DCS are utilized for preparation of 1,6-hexanediol. For example, the 6-oxocaproic acid present is lost in the process and also reduces, as a result of high boiler formation, the distillation yields of intermediate esters for preparation of 1,6-hexanediol. Moreover, the 1,6-hexanediol is not entirely free of undesired 1,4-cyclohexanediols, since they are removed efficiently as such in the process, but get into the hydrogenation as 4-hydroxycyclohexanone and give rise there to 1,4-cyclohexanediols in turn, which can be removed from 1,6-hexanediol only with difficulty. In addition, conversion products of 6-oxocaproic acid are detectable in the 1,6-hexanediol, for example 6,6-dimethoxyhexan-1-ol and 6-methoxyhexan-1-ol. These monoalcohols are generally very troublesome in polymer applications of diols, since they block one end in the course of chain formation. A further disadvantage is that the formic acid present in the DCS causes corrosion problems in the removal of water before the esterification stage, such that premium, expensive materials have to be used.

It was therefore an object of the present invention to provide a process for preparing 1,6-hexanediol, which enables, even proceeding from highly complex dicarboxylic acid solutions, the linear C6 carboxylic acids present therein to be converted as completely as possible to prepare very pure 1,6-hexanediol, and hence the same or higher purity of the products to be achieved as known from the preparation process proceeding from pure adipic acid, without requiring additional and costly purification steps and/or materials.

Figure 1:
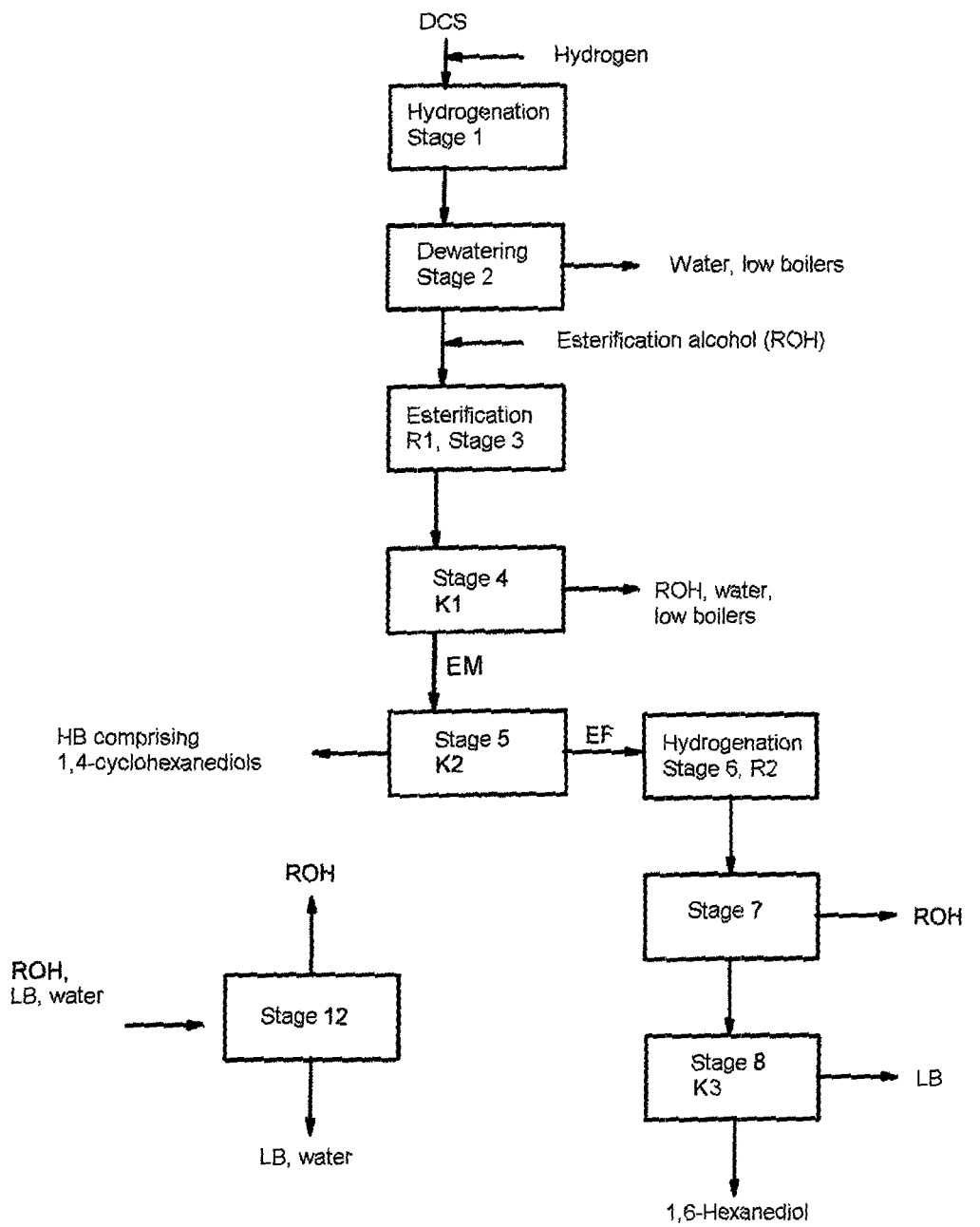
FIG. 1 is a flowchart illustrating the process according to the invention.

This object is achieved by a process for preparing 1,6-hexanediol from a carboxylic acid mixture which comprises adipic acid, 6-hydroxycaproic acid, 6-oxocaproic acid, 4-hydroxycyclohexanone, formic acid and, based on the sum of adipic acid and hydroxycaproic acid, between 0.5 and 5% by weight of 1,4-cyclohexanediols, and is obtained as a by-product of the catalytic oxidation of cyclohexane to cyclohexanone/cyclohexanol with oxygen or oxygen-comprising gases by water extraction of the reaction mixture, by esterifying and hydrogenating a substream to hexanediol, which comprises a) hydrogenating only the aldehydes and ketones present in the aqueous carboxylic acid mixture catalytically to the corresponding alcohols and hydrogenating any C—C double bonds present to the corresponding saturated compounds and degrading more than 50% by weight of the formic acid present in the mixture, b) reacting the mono- and dicarboxylic acids present in the aqueous reaction mixture, after dewatering, with a low molecular weight alcohol to give the corresponding carboxylic esters, c) freeing the resulting esterification mixture of excess alcohol and low boilers in a first distillation stage, d) in a second distillation stage, performing a separation of the bottom product into an ester fraction depleted of 1,4-cyclohexanediols and a fraction comprising 1,4-cyclohexanediols, e) catalytically hydrogenating the ester fraction from (d), and obtaining 1,6-hexanediol in a manner known per se by distilling the hydrogenation product.

The hydrogenation of a DCS is very complex since many compounds which can disrupt the actual hydrogenation or are likewise hydrogenated are present, which can complicate the subsequent workup. It was not trivial but surprising that the hydrogenation of the aldehydes in step a) was so selective that the C6-hydroxycarboxylic acids present in the DCS were not already converted to 1,6-hexanediol in this step. Had this been the case, the 1,6-hexanediol formed would subsequently be removed together with the 1,4-cyclohexanediols in step d) of the process according to the invention, thus reducing the yield of 1,6-hexanediol. In addition, it was surprising that the catalyst used, in spite of the corrosive medium, has a high lifetime, and it was possible to lower the formation of high boilers in the process to such an extent that the yield and purity of 1,6-hexanediol was improved significantly. Furthermore, it was not foreseeable that formic acid was degraded at least to an extent of 50%, and hence downstream stages are less affected by corrosion.

The esterification can be performed without addition of catalysts, but preferably under the action of catalysts. Useful low molecular weight alcohols are generally those having 1 to 10 carbon atoms, especially alkanols having 1 to 8 carbon atoms. Diols such as butanediol or pentanediol are also useful in principle.

The industrially preferred alcohols for use for the esterification are n- or i-butanol and especially methanol.

In the case of esterification with methanol, the procedure is to obtain, in the distillation stage (d), a methyl carboxylate fraction freed of 1,4-cyclohexanediols at the top of the column, and a bottom fraction comprising the high boilers and the 1,4-cyclohexanediols, and to catalytically hydrogenate the methyl carboxylate fraction in the hydrogenation stage (e).

In the process according to the invention, terms such as "via the top" or "via the bottom" each mean, respectively, removal above and below the feed of a distillation unit such as a column.

As shown in FIG. 1, the dicarboxylic acid solution (DCS) is hydrogenated, dewatered, then fed together with a $C_1$- to $C_3$-alcohol, preferably methanol, into the esterification reactor $R_1$ in which the carboxylic acids are esterified. The esterification mixture obtained then passes into the column $K_1$ in which the excess alcohol (ROH), water and low boilers (LB) are distilled off via the top, and the ester mixture (EM) is drawn off as bottoms and fed into column $K_2$. In this column, the EM is fractionated into an ester fraction (EF) which has been predominantly freed of 1,4-cyclohexanediols (a maximum of 5% by weight, preferably less than 1% by weight, of the 1,4-cyclohexanediols present in the feed) and a bottom fraction consisting of high boilers (HB) and cis- and trans-1,4-cyclohexanediols (1,4-CHDO). The ester fraction is then hydrogenated to 1,6-hexanediol and esterification alcohol, and 1,6-hexanediol is purified by distillation in $K_3$.

Figure 2:
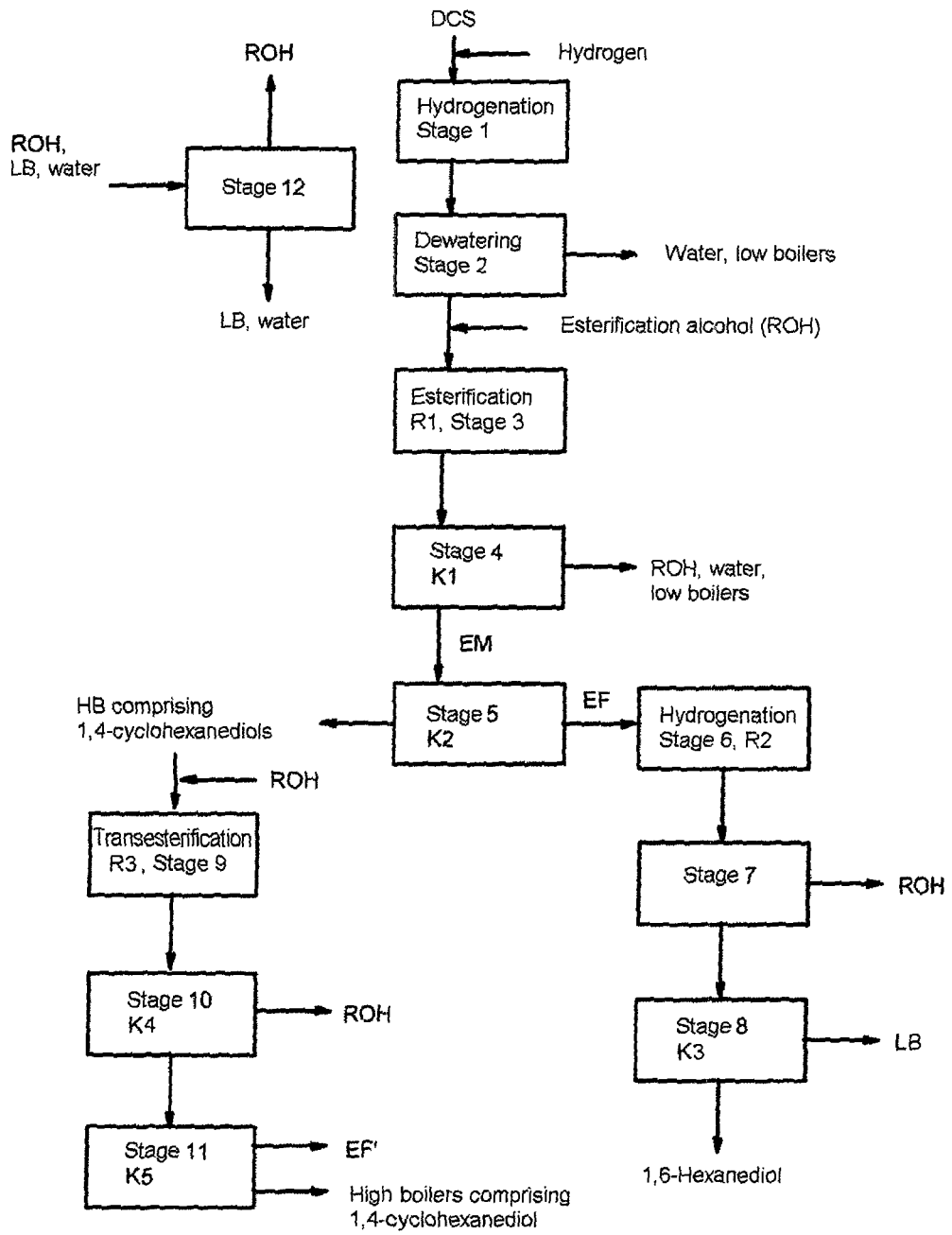
FIG. 2 is a flowchart illustrating the process according to the invention, including an additional reaction of the high boiler mixture obtained in column 2 with esterification alcohol, and subsequent separation.

To enhance the overall yield of C6 products of value, as described in FIG. 2, the high boiler mixture obtained in column 2 can additionally be reacted once again with esterification alcohol ROH (R3), then freed of excess alcohol ROH in a further column $K_4$, and separated in a column $K_5$ into high boilers which comprise the 1,4-cyclohexanediols and a further ester mixture EF'. This EF' can, for example, be fed back into column $K_2$ together with the ester mixture EM.

The process according to the invention is explained in detail hereinafter with reference to FIGS. 1 and 2.

The process steps are broken down into stages, stages 1, 2, 3, 4, 5, 6, 7 and 8, and 12, being essential to the process, and stages 4 and 5, and 7 and 8, also being combinable. Stages 9, 10 and 11 are optional, but may be advisable to increase the economic viability of the process.

For the catalytic hydrogenation of the DCS in step a) of the process according to the invention (stage 1), catalysts which comprise at least one metal of groups 7 to 12 of the periodic table, for example ruthenium, palladium, platinum, nickel, cobalt, iron, rhenium, iridium, copper, osmium and zinc, are used.

Preference is given to the metals ruthenium, nickel, cobalt, rhenium and copper. These metals can be used here in the form of the metals or of the compounds thereof, for example oxides and sulfides.

Preference is further given to mixtures or alloys of at least two of the metals of groups 7 to 12 of the periodic table. Examples include palladium/rhenium, platinum/rhenium and cobalt/copper.

Additionally very suitable are what are known as unsupported catalysts, which do not comprise a support and consist of metals, metal oxides or mixtures thereof. Preference is given to unsupported iron and especially cobalt catalysts.

The metals or metal compounds can be used without support. However, they are preferably applied to supports, for example $TiO_2$, $Al_2O_3$, $ZrO_2$, $SiO_2$, $HfO_2$, carbon, zeolites or mixtures thereof. These supported catalysts can be used in a wide variety of different finished forms, for example extrudates, tablets or rings.

Copper, nickel and cobalt can preferably be used in the form of Raney nickel, Raney copper or Raney cobalt. The Raney catalysts can also be used in all known finished forms, for example as tablets, extrudates or granules. Suitable Raney copper catalysts are, for example, Raney copper nuggets which are described in WO-A 99/03801.

Also particularly suitable for the hydrogenation of the DCS is a catalyst comprising ruthenium supported on shaped titanium dioxide bodies, the shaped titanium dioxide bodies being obtained by treating titanium dioxide, before or after shaping to the shaped body, with 0.1 to 30% by weight of an acid in which titanium dioxide is sparingly soluble.

The catalytically active ruthenium is applied by processes known per se, preferably to prefabricated $TiO_2$ as a support material.

A titanium dioxide support suitable with preference for use in the ruthenium-comprising catalyst can be obtained according to DE-A 197 38 464 by treating titanium dioxide, before or after the shaping of the shaped body, with 0.1 to 30% by weight of an acid, based on titanium dioxide, in which the titanium dioxide is sparingly soluble. Preference is given to using titanium dioxide in the anatase polymorph. Suitable acids of this kind are, for example, formic acid, phosphoric acid, nitric acid, acetic acid or stearic acid.

The active ruthenium component can be applied in the form of a ruthenium salt solution to the titanium dioxide support thus obtained in one or more impregnation stages. Subsequently, the impregnated support is dried and optionally calcined. It is, however, also possible to precipitate ruthenium out of a ruthenium salt solution, preferably with sodium carbonate, onto a titanium dioxide present in the form of powder in aqueous suspension. The precipitated solids are washed, dried, optionally calcined and shaped. In addition, volatile ruthenium compounds, for example ruthenium acetylacetonate or ruthenium carbonyl, can be converted to the gas phase and applied to the support in a manner known per se, which is referred to as chemical vapor deposition.

Other preferred support materials are zirconium oxide, silicon carbide and carbon. Especially carbon (activated carbons) has the advantage of low liter weight with simultaneously high surface area and chemical resistance to acids. The carbon supports can, before use, be pretreated oxidatively with, for example, air or nitric acid; likewise suitable is treatment with strong acids such as sulfuric acid, hydrochloric acid or phosphoric acid. The pretreatment generally leads to higher catalytic activity.

The supported catalysts thus obtained may be present in all known finished forms. Examples are extrudates, tablets or granules. Before they are used, the ruthenium catalyst precursors are reduced by treatment with hydrogenous gas, preferably at temperatures greater than 100° C. Before they are used in the process according to the invention, the catalysts are preferably passivated at temperatures of 0 to 50° C., preferably at room temperature, with oxygenous mixtures, preferably with air-nitrogen mixtures. It is also possible to install the catalyst into the hydrogenation reactor in oxidic form and to reduce it under reaction conditions.

The catalyst which is particularly preferred in accordance with the invention has a ruthenium content of 0.01 to 10% by weight, preferably of 0.1 to 6% by weight, based on the total weight of the catalyst composed of catalytically active metal and support. The inventive catalyst may have a sulfur content of 0.01 to 1% by weight, based on the total weight of the catalyst, the sulfur being determined by coulometric means.

The ruthenium surface area is from 1 to 20 m$^2$/g, preferably from 5 to 15 m$^2$/g, and the BET surface area (determined to DIN 66 131) from 5 to 500 m$^2$/g, preferably from 50 to 200 m$^2$/g.

The inventive catalysts have a pore volume of 0.1 to 100 ml/g. In addition, the catalysts feature a cutting hardness of 1 to 100 N.

The hydrogenation catalysts may be suspended in the reaction mixture. They are preferably arranged in fixed bed form in the hydrogenation reactor. The hydrogenation can be performed batchwise or preferably continuously. The reaction mixture can be passed over the catalyst in liquid phase mode or trickle mode.

The hydrogenation can be performed in a single reactor or in two series-connected reactors. When two reactors are used, the two reactors may comprise the same catalyst or two different catalysts. The two reactors may differ in the hydrogenation temperature and the partial hydrogen pressure.

It is additionally possible to perform the hydrogenation in a single reactor filled with a single catalyst, in such a way that the hydrogenation temperature in the reactor rises within a desired temperature range. The temperature range for the hydrogenation is between 50 and 200° C., preferably 70 to 180° C., more preferably between 90 and 160° C.

The reaction pressure, essentially generated by hydrogen, is between 1 and 100 bar absolute, preferably 3 to 50 bar, more preferably between 5 and 35 bar.

The hydrogen used may be pure hydrogen, but it is also possible, for industrial purposes even preferred, to completely or at least partly use the offgas from another hydrogenation, for example that of the esters to 1,6-hexanediol, for the hydrogenation.

The molar excess of hydrogen based on the component to be hydrogenated is between 1 and 5000 mol %, preferably 10 to 3000 mol %, more preferably 50 to 1000 mol %.

The dicarboxylic acid solution (DCS) is generally an aqueous solution with a water content of 20 to 80% by weight.

Since an esterification reaction is an equilibrium reaction in which water forms, it is advisable, especially in the case of esterification with, for example, methanol, to remove water present before the reaction, in particular when water cannot be removed, for example azeotropically, during the esterification reaction. The dewatering (stage 2) in step b) can be effected, for example, with a membrane system, or preferably by means of a distillation apparatus in which water is removed via the top, and higher monocarboxylic acids, dicarboxylic acids and 1,4-cyclohexanediols via the bottom, at 10 to 250° C., preferably 20 to 200° C., more preferably 30 to 200° C., and a pressure of 1 to 1500 mbar, more preferably 5 to 1100 mbar, most preferably 20 to 1000 mbar. The bottom temperature is preferably selected such that the bottom product can be drawn off in liquid form. The water content in the bottom of the column may be 0.01 to 10% by weight, preferably 0.01 to 5% by weight, more preferably 0.01 to 1% by weight.

The water can be removed in such a way that the water is obtained in acid-free form, or the lower monocarboxylic acids present in the DCS—essentially formic acid if still present—can be distilled off for the most part with the water, preferably 60-95% by weight of the acids present in the feed, such as formic acid and acetic acid, in order that they do not bind any esterification alcohol in the esterification. Together with the water, it is also possible to remove further components, for example cyclohexanol, any cyclohexanone still present. These can be separated from water, for example, by phase separation and be released as products of value, for example, into the cyclohexanol/cyclohexanone recovery.

Alcohol ROH having 1 to 10 carbon atoms is added to the carboxylic acid stream from stage 2. It is possible to use methanol, ethanol, propanol or isopropanol, or mixtures of the alcohols, but preferably methanol on the one hand, or $C_4$ and higher alcohols, especially having 4 to 8 carbon atoms and preferably n- or i-butanol or else n-pentanol or i-pentanol on the other hand. The mixing ratio of alcohol to carboxylic acid stream (mass ratio) may be from 0.1 to 30, preferably 0.2 to 20, more preferably 0.5 to 10.

This mixture passes as a melt or solution into the reactor of stage 3, in which the carboxylic acids are esterified with the alcohol. The esterification reaction can be performed at 50 to 400° C., preferably 70 to 300° C., more preferably 90 to 200° C. It is possible to apply an external pressure, but preference is given to performing the esterification under autogenous pressure of the reaction system. The esterification apparatus used may be a stirred tank or flow tube, or it is possible to use a plurality of each. The residence time needed for the esterification is between 0.3 and 10 hours, preferably 0.5 to 5 hours. The esterification reaction can proceed without addition of a catalyst, but preference is given to adding a catalyst to increase the reaction rate. This may be a homogeneous dissolved catalyst or a solid catalyst. Examples of homogeneous catalysts include sulfuric acid, phosphoric acid, hydrochloric acid, sulfonic acids such as p-toluenesulfonic acid, heteropolyacids such as tungstophosphoric acid, or Lewis acids, for example aluminum, vanadium, titanium and boron compounds. Preference is given to mineral acids, especially sulfuric acid. The weight ratio of homogeneous catalyst to carboxylic acid melt is generally 0.0001 to 0.5, preferably 0.001 to 0.3.

Suitable solid catalysts are acidic or superacidic materials, for example acidic and superacidic metal oxides such as $SiO_2$, $Al_2O_3$, $SnO_2$, $ZrO_2$, sheet silicates or zeolites, all of which may be doped with mineral acids such as sulfate or phosphate for acid strengthening, or organic ion exchangers with sulfonic acid or carboxylic acid groups. The solid catalysts may be arranged as a fixed bed or be used as a suspension.

The water formed in the reaction is appropriately removed continuously, for example by means of a membrane or distillation.

The completeness of the conversion of the free carboxyl groups present in the carboxylic acid melt is determined with the acid number (mg KOH/g) measured after the reaction. Minus any acid added as a catalyst, it is 0.01 to 50, preferably 0.1 to 10. Not all carboxyl groups present in the system need be present as esters of the alcohols used, but a portion thereof may instead be present in the form of dimeric or oligomeric esters with the OH end of the hydroxycaproic acid.

The esterification mixture is fed into stage 4, a membrane system or preferably a distillation column. When a dissolved acid was used as the catalyst for the esterification reaction, the esterification mixture is appropriately neutralized with a base, in which case 1 to 1.5 base equivalents are added per acid equivalent of the catalyst. The bases used are generally alkali metal or alkaline earth metal oxides, carbonates, hydroxides or alkoxides, or amines in substance or dissolved in the esterification alcohol. It is likewise possible to use ion exchangers, which are preferably reusable time and again by regeneration.

When a column is used in stage 4, the feed to the column is preferably between the top stream and the bottom stream. The excess esterification alcohol ROH, water and corresponding esters of formic acid, acetic acid and propionic acid are drawn off via the top at pressures of 1 to 1500 mbar, preferably 20 to 1000 mbar, more preferably 40 to 800 mbar, and temperatures between 0 and 150° C., preferably 15 and 90° C. and especially 25 and 75° C. This stream can either be combusted or preferably worked up further in stage 12.

The bottoms obtained are an ester mixture which consists predominantly of the esters of the alcohol ROH used with dicarboxylic acids such as adipic acid and glutaric acid, hydroxycarboxylic acids such as 6-hydroxycaproic acid and 5-hydroxyvaleric acid, and of oligomers and free or esterified 1,4-cyclohexanediols. It may be advisable to permit a residual content of water and/or alcohol ROH up to 4% by weight each in the ester mixture. The bottom temperatures are 70 to 250° C., preferably 80 to 220° C., more preferably 100 to 190° C.

The stream from stage 4, which has been substantially freed of water and esterification alcohol ROH, is fed into stage 5. This is a distillation column in which the feed is between the low-boiling components and the high-boiling components. The column is operated at temperatures of 10 to 300° C., preferably 20 to 270° C., more preferably 30 to 250° C., and pressures of 1 to 1000 mbar, preferably 5 to 500 mbar, more preferably 10 to 200 mbar.

The top fraction consists predominantly of residual water and residual alcohol ROH, esters of the alcohol ROH with monocarboxylic acids, predominantly $C_3$- to $C_6$-monocarboxylic esters with hydroxycarboxylic acids such as 6-hydroxycaproic acid, 5-hydroxyvaleric acid, and in particular the diesters with dicarboxylic acids such as adipic acid, glutaric acid and succinic acid, and 1,2-cyclohexanediols, caprolactone and valerolactone.

The components mentioned may be removed together via the top or, in a further preferred embodiment, be separated in the column of stage 5 into a top stream comprising predominantly residual water and residual alcohol and the abovementioned constituents having 3 to 5 carbon atoms, and a sidestream comprising predominantly the abovementioned constituents of the $C_6$ esters. The stream comprising the esters of the $C_6$ acids can pass entirely into the hydrogenation (stage 6).

The high-boiling components of the stream from stage 4, predominantly consisting of 1,4-cyclohexanediols or esters thereof, dimeric or oligomeric esters and constituents of the DSC, some of them polymeric, which are not defined in detail, are removed via the stripping section of the column of stage 5. These may be obtained together or in such a way that predominantly the 1,4-cyclohexanediols are removed via a sidestream of the column in the stripping section and the rest via the bottom. The 1,4-cyclohexanediols thus obtained may find use, for example, as a starting material for active ingredients. The high-boiling components, with or without the 1,4-cyclodiol content, can be incinerated.

Stages 4 and 5 can, especially when only relatively small amounts are processed, be combined. To this end, for example, the $C_6$ ester stream can be obtained in a fractional distillation performed batchwise, again without 1,4-cyclohexanediols getting into the stream conducted to the hydrogenation.

The hydrogenation is effected catalytically either in the gas or liquid phase. Useful catalysts in principle include all homogeneous and heterogeneous catalysts suitable for hydrogenation of carbonyl groups, such as metals, metal oxides, metal compounds or mixtures thereof. Examples of homogeneous catalysts are described in H. Kropf, Houben-Weyl, Methoden der Organischen Chemie [Methods of Organic Chemistry], volume IV/1c, Georg Thieme Verlag Stuttgart, 1980, p. 45 to 67, and examples of heterogeneous catalysts are described in Houben-Weyl, Methoden der Organischen Chemie, volume IV/1c, p. 16 to 26.

Preference is given to using catalysts which comprise one or more of the elements from transition groups I and VI to VIII of the periodic table of the elements, preferably copper, chromium, molybdenum, manganese, rhenium, ruthenium, cobalt, nickel and palladium, more preferably copper, cobalt or rhenium.

The catalysts may consist solely of the active components, or the active components may be applied to supports. Suitable support materials are, for example, $Cr_2O_3$, $Al_2O_3$, $SiO_2$, $ZrO_2$, $TiO_2$, $ZnO_2$, $BaO$ or $MgO$ or mixtures thereof.

Particular preference is given to catalysts as described in EP 0 552 463. These are catalysts which possess, in the oxidic form, the composition

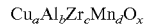

where a>0, b>0, c≧0, d>0, a>b/2, b>a/4, a>c, a>d, and x denotes the number of oxygen ions required per formula unit to provide electrical neutrality. These catalysts can be prepared, for example, according to specifications of EP 0 552 463 by precipitation of sparingly soluble compounds from solutions which comprise the corresponding metal ions in the form of salts thereof. Suitable salts are, for example, halides, sulfates and nitrates. Suitable precipitants are all agents which lead to the formation of such insoluble intermediates, which can be converted to the oxides by thermal treatment. Particularly suitable intermediates are the hydroxides and carbonates or hydrogencarbonates, and so the particularly preferred precipitants used are alkali metal carbonates or ammonium carbonate. An important feature for the preparation of the catalysts is the thermal treatment of the intermediates at temperatures between 500° C. and 1000° C. The BET surface area of the catalysts is between 10 and 150 $m^2/g$.

Further preferred hydrogenation catalysts comprise, as well as Cu, also lanthanum and aluminum oxides. They are described, for example, in DE-A 10313702.

Preference is given to using heterogeneous catalysts which are either arranged in fixed bed form or used as a suspension. When the hydrogenation is performed in the gas phase and over catalyst arranged in fixed bed form, temperatures of 150 to 300° C. are generally employed at pressures of 1 to 100 bar, preferably 15 to 70 bar. Appropriately, at least a sufficient amount of hydrogen as a hydrogenating agent and carrier gas is used that reactants, intermediates and products never become liquid during the reaction. The excess hydrogen is preferably circulated, in which case a small portion can be discharged as offgas to remove inerts, for example methane. It is possible to use one reactor or a plurality of reactors connected in series.

When the hydrogenation is effected in the liquid phase with fixed bed or suspended catalyst, it is generally performed at temperatures between 100 and 350° C., preferably 120 and 300° C., and pressures of 30 to 350 bar, preferably 40 to 300 bar.

The hydrogenation can be performed in one reactor or a plurality of reactors connected in series. The hydrogenation in the liquid phase over a fixed bed can be performed either in trickle mode or liquid phase mode. In a preferred embodiment, a plurality of reactors are used, in which case the predominant portion of the esters is hydrogenated in the first reactor and the first reactor is preferably operated with liquid circulation for heat removal and the downstream reactor(s) is/are preferably operated without circulation to complete the conversion. Cycle gas is unnecessary especially in trickle mode.

The hydrogenation can be performed batchwise, preferably continuously.

The hydrogenation output consists essentially of 1,6-hexanediol and the alcohol ROH. Further constituents are in particular, if the overall low-boiling stream of stage 5 was used, 1,5-pentanediol, 1,4-butanediol, 1,2-cyclohexanediols and small amounts of monoalcohols having 1 to 6 carbon atoms, optionally ethers and water.

The hydrogenation output is separated in stage 7, for example a membrane system or preferably a distillation column, into the alcohol ROH which additionally comprises the majority of the further low-boiling components and a stream which comprises predominantly 1,6-hexanediol in addition to 1,5-pentanediol and the 1,2-cyclohexanediols. Top temperatures of 0 to 120° C., preferably 20 to 100° C., more preferably 30 to 90° C., and bottom temperatures of 100 to 270° C., preferably 140 to 260° C., more preferably 160 to 250° C., are established at a pressure of 10 to 1500 mbar, preferably 30 to 1200 mbar, more preferably 50 to 1000 mbar. The low-boiling stream can either be returned directly into the esterification of stage 3 or pass into stage 9 or into stage 12.

The stream comprising 1,6-hexanediol is purified in a column in stage 8. In this purification, 1,5-pentanediol, the 1,2-cyclohexanediols and any further low boilers present are removed via the top. If the 1,2-cyclohexanediols and/or 1,5-pentanediol are to be obtained as additional products of value, they can be separated in a further column. Any high boilers present are discharged via the bottom. 1,6-Hexanediol with a purity of at least 99.5%, preferably at least 99.7%, more preferably more than 99.9%, is withdrawn from a sidestream of the column. Top temperatures of 50 to 200° C., preferably 60 to 150° C., and bottom temperatures of 130 to 270° C., preferably 150 to 250° C., are established at pressures of 1 to 1000 mbar, preferably 5 to 800 mbar, more preferably 20 to 500 mbar.

If only small amounts of 1,6-hexanediol are to be prepared, stages 7 and 8 can also be combined in a batchwise fractional distillation.

In order to operate the process according to the invention in a very economically viable manner, it is advisable to recover the esterification alcohol ROH and to use it time and again for the esterification. To this end, the stream comprising predominantly the alcohol ROH from stage 4 and/or 7 can be worked up in stage 12. To this end, it is advantageous to use a column in which lower-boiling components than the alcohol ROH are removed via the top, and water and higher-boiling components than the alcohol ROH are removed via the bottom, from the alcohol ROH which is obtained in a sidestream. The column is appropriately operated at 500 to 5000 mbar, preferably at 800 to 3000 mbar.

In a further preferred embodiment of the process according to the invention, the high-boiling stream from stage 5 is worked up to increase the overall yield of products of value, based on the DCS used. To this end, in stage 9, the proportion of dimeric and oligomeric esters of adipic acid or hydroxycaproic acid is reacted with further amounts of the alcohol ROH, preferably methanol, in the present of a catalyst. The weight ratio of alcohol ROH and the bottom stream from stage 5 is between 0.1 and 20, preferably 0.5 to 10, more preferably 1 to 5. Suitable catalysts are in principle those already described for the esterification in stage 3. Preference is given, however, to using Lewis acids or Lewis bases. Examples thereof are compounds or complexes of aluminum, tin, antimony, zirconium or titanium, such as zirconium acetylacetonate or tetraalkyl titanate such as tetraisopropyl titanate, which are employed in concentrations of 1 to 10 000 ppm, preferably 50 to 6000 ppm, more preferably 100 to 4000 ppm. Particular preference is given to titanium compounds.

The transesterification can be performed batchwise or continuously, in one reactor or a plurality of reactors, in series-connected stirred tanks or tubular reactors, at temperatures between 100 and 300° C., preferably 120 to 270° C., more preferably 140 to 240° C., and the autogenous pressures which are established. The residence times required are 0.5 to 10 hours, preferably 1 to 4 hours.

In the case of esterification with methanol, this stream from stage 9 can be fed, for example, back into stage 4. To prevent accumulations, in particular of 1,4-cyclohexanediols, a substream of the high boilers from stage 5 must then be discharged batchwise or continuously. Another option is to recycle the stream from stage 9 not into stage 4, but to separate it, analogously to stage 4, in a stage 10 into predominantly alcohol ROH, which can then pass back into stage 3, 9 or 12, and a stream which comprises the esters.

This ester stream can in principle (with the proviso of preventing accumulations of the 1,4-cyclohexanediols) be recycled into stage 5, or is preferably separated in a further stage 11 into the esters of the $C_6$ acids and, in a relatively insignificant amount, into the esters of the $C_5$ acids on the one hand, which are either fed into stage 5 or directly into stage 6, and high boilers on the other hand, which comprise 1,4-cyclohexanediols, and then the high boilers are discharged.

In the process according to the invention, yields of 1,6-hexanediol of more than 95% can be achieved with purities of more than 99%.

The process is illustrated in detail with reference to the examples which follow, but is not restricted in any way as a result. The figures regarding the composition of the streams are % by weight determined by gas chromatography.

EXAMPLE 1

Comparative Example without Hydrogenation of the DCS

Stage 2: (Dewatering)

0.1 kg of dicarboxylic acid solution/h (adipic acid, 6-hydroxycaproic acid, 6-oxocaproic acid, 1,4-cyclohexanediols, 4-hydroxycyclohexanone, glutaric acid, 5-hydroxyvaleric acid, formic acid, water) was distilled continuously in a distillation apparatus (three-tray bubble-cap tray column with external oil heating circuit, oil temperature 150° C., tray volume approx. 25 ml each, feed via the bubble-cap trays) with an attached column with random packing (approx. 4 theoretical plates, no return stream at the top). The top product obtained was 0.045 kg with a formic acid content in water of approx. 3%. The water content in the bottom stream (5.5 kg) was approx. 0.4%.

Stage 3: (Esterification)

5.5 kg of the bottom stream from stage 1 were reacted with 8.3 kg of methanol and 14 g of sulfuric acid. The acid number of the output minus sulfuric acid was approx. 10 mg KOH/g.

Stage 4:

In a column, the esterification stream from stage 2 was distilled (1015 mbar, top temperature 65° C., bottom temperature up to 125° C.). 7.0 kg were drawn off via the top. The bottom product obtained was 6.8 kg.

Stage 5: (1,4-Cyclohexanediol removal)

In a 50 cm column with random packing, the bottom stream from stage 3 was fractionally distilled (10 mbar, top temperature 75-90° C., bottom temperature up to 200° C.). The 1,4-cyclohexanediols were found in the bottoms.

The low boilers distilled off were 0.3 kg (dimethyl succinate, methyl valerate, methyl pentanoate, methyl caproate, 1,2-cyclohexanediols, valerolactone, methyl 5-hydroxyvalerate, dimethyl glutarate, among others); as the fraction comprising predominantly dimethyl adipate and methyl 6-hydroxycaproate, 4.6 kg were obtained, which also comprised between 2 and 5% dimethyl glutarate and methyl 5-hydroxyvalerate, between 0.2 and 1% valerolactone, caprolactone, methyl 6,6-dimethoxycaproate and 4-hydroxycyclohexanone.

Stage 6: (Substream hydrogenation)

2.7 kg of $C_6$ ester mixture from stage 5 were hydrogenated continuously over a catalyst in a 25 ml reactor (catalyst: 70% by weight of CuO, 25% by weight of ZnO, 5% by weight of $Al_2O_3$, which has been activated beforehand in a hydrogen stream at 180° C., hydrogenation conditions: feed 20 g/h, no circulation, 220 bar, 220° C.). The ester conversion was 99.5%; the 1,6-hexanediol selectivity was more than 99%.

Stages 7 and 8: (Hexanediol purification)

2.5 kg of the hydrogenation output from stage 6 were fractionally distilled (distillation still with attached 70 cm column with random packing, reflux ratio 2). At 1013 mbar, 0.5 kg of methanol was distilled off and, after applying vacuum (20 mbar), predominantly the 1,2-cyclohexanediols and 1,5-pentanediol distilled off. Thereafter (b.p. 146° C.), 1,6-hexanediol distilled off with a purity of 99.6%. In addition to quantitatively insignificantly components, approx. 0.2% 1,4-cyclohexanediols and approx. 0.02% 6-methoxyhexan-1-ol and 0.1% 6,6-dimethoxyhexan-1-ol were found in the hexanediol.

EXAMPLE 2

Inventive Example

Stage 1: (DCS Hydrogenation)

0.1 kg/h of dicarboxylic acid solution was hydrogenated in a tubular reactor (length 1 m, capacity 100 ml) at 120° C. and hydrogen pressure 20 bar, 25 standard liters of hydrogen/h over 100 ml of an Ru (5%)/titanium dioxide catalyst. The hydrogenation was conducted for 500 h without the composition of the hydrogenation output changing significantly. The 1,6-hexanediol content after the hydrogenation was less than 0.1% higher than before the hydrogenation.

Stage 2: (Dewatering)

0.1 kg/h of dicarboxylic acid solution from stage 1 (adipic acid, 6-hydroxycaproic acid, 1,4-cyclohexanediols, glutaric acid, 5-hydroxyvaleric acid, formic acid, water) was distilled continuously in a distillation apparatus (three-tray bubble-cap tray column with external oil heating circuit, oil temperature 150° C., tray volume approx. 25 ml each, feed via the bubble-cap tray) with an attached column with random packing (approx. 4 theoretical plates, no return stream at the top). The top product obtained was 0.04 kg with a formic acid content in water of approx. 0.2%. In the bottom stream (5.5 kg), the water content was approx. 0.4%.

The comparison between the comparative example and the inventive example shows a significantly smaller amount of formic acid, as a result of which a purer end product (see stage 7/8) than known in the prior art is obtained.

Stage 3: (Esterification)

5.5 kg of the bottom stream from stage 1 were reacted with 8.3 kg of methanol and 14 g of sulfuric acid. The acid number of the output minus sulfuric acid was approx. 10 mg KOH/g.

Stage 4:

In a column, the esterification stream from stage 2 was distilled (1015 mbar, top temperature 65° C., bottom temperature up to 125° C.). 7.0 kg were drawn off via the top. The bottom product obtained was 6.8 kg.

Stage 5: (1,4-Cyclohexanediol Removal)

In a 50 cm column with random packing, the bottom stream from stage 3 was fractionally distilled (10 mbar, top temperature 75-90° C., bottom temperature up to 200° C.). The 1,4-cyclohexanediols were found in the bottoms.

The low boilers distilled off were 0.3 kg (dimethyl succinate, methyl valerate, methyl pentanoate, methyl caproate, 1,2-cyclohexanediols, valerolactone, methyl 5-hydroxyvalerate, dimethyl glutarate, among others); as the fraction comprising predominantly dimethyl adipate and methyl 6-hydroxycaproate, 5.5 kg were obtained, which also comprised between 2 and 5% dimethyl glutarate and methyl 5-hydroxyvalerate, between 0.2 and 1% valerolactone and caprolactone.

Stage 6: (Substream Hydrogenation)

3 kg of $C_6$ ester mixture from stage 5 were hydrogenated continuously over a catalyst in a 25 ml reactor (catalyst: 70% by weight of CuO, 25% by weight of ZnO, 5% by weight of $Al_2O_3$, which has been activated beforehand in a hydrogen stream at 180° C., hydrogenation conditions: feed 20 g/h, no circulation, 220 bar, 220° C.). The ester conversion was 99.5%; the 1,6-hexanediol selectivity was more than 99%.

Stages 7 and 8: (Hexanediol Purification)

2.9 kg of the hydrogenation output from stage 6 were fractionally distilled (distillation still with attached 70 cm column with random packing, reflux ratio 2). At 1013 mbar, 0.6 kg of methanol was distilled off and, after applying vacuum (20 mbar), predominantly the 1,2-cyclohexanediols and 1,5-pentanediol distilled off. Thereafter (b.p. 146° C.), 1,6-hexanediol distilled off with a purity of 99.93%. In the hexanediol, in addition to quantitatively insignificantly components, only approx. 0.01% 1,4-cyclohexanediols was found. 6-Methoxyhexan-1-ol and 6,6-dimethoxyhexan-1-ol were not found.

EXAMPLE 3

Example 2 stage 1 was repeated, with the difference that the catalyst used was Ru (0.5%) on activated carbon. The hydrogenation result was equivalent to example 2.

EXAMPLE 4

Example 2 stage 1 was repeated, with the difference that the catalyst used was Ni (10%) on activated carbon at 150° C. and 50 bar. The hydrogenation result was equivalent to example 2.

EXAMPLE 5

Example 2 stage 1 was repeated, with the difference that the catalyst used was Co (10%) on activated carbon at 120° C. and 50 bar. The hydrogenation result was equivalent to example 2.

The invention claimed is:

1. A process for preparing 1,6-hexanediol from a first carboxylic acid mixture the process comprising
    (a) hydrogenating only any aldehyde or ketone present in an aqueous carboxylic acid mixture catalytically to a corresponding alcohol at a hydrogenation temperature of from 50 to 200° C. and a reaction pressure of from 5 to 35 bar absolute and degrading more than 50% of formic acid present in the mixture; to obtain a second aqueous mixture,
    (b) reacting any monocarboxylic acid or dicarboxylic acid present in the second aqueous reaction mixture, after dewatering, with a low molecular weight alcohol to give a corresponding carboxylic ester, in an esterification mixture;
    (c) freeing the esterification mixture of excess alcohol and low boilers in a first distillation stage, to obtain a bottom product;
    (d) in a second distillation stage, performing a separation of the bottom product into an ester fraction depleted of at least one 1,4-cyclohexanediol and a second fraction comprising at least one 1,4-cyclohexanediol;
    (e) catalytically hydrogenating the ester fraction from (d), and obtaining 1,6 hexanediol by distilling the hydrogenation product,
    wherein the first carboxylic acid mixture comprises:
    adipic acid;
    6-hydroxycaproic acid;
    6 oxocaproic acid:,
    4 hydroxycyclohexanone;
    formic acid; and,
    based on a sum of adipic acid and hydroxycaproic acid, between 0.5 and 5% by weight of at least one 1,4-cyclohexanediol, and
    wherein the first carboxylic acid mixture is obtained as a by-product of a catalytic oxidation of cyclohexane to cyclohexanone/cyclohexanol with oxygen or at least one oxygen-comprising gas by water extraction of a reaction mixture from the oxidation.

2. The process of claim 1, wherein a catalyst for the hydrogenating in (a) comprises at least one metal selected from the group consisting of ruthenium, nickel, cobalt, rhenium, and copper, in the form of a metal or a compound thereof.

3. The process of claim 1, wherein a catalyst for the hydrogenating in (a) comprises ruthenium, cobalt, or nickel, supported on shaped titanium dioxide or at least one activated carbon body.

4. The process of claim 3, wherein the catalyst for the hydrogenating in (a) has a metal content in a range from 0.01 to 10% by weight based on a total weight of the catalyst based on any catalytically active metals and support, and a BET surface area in a range from 5 to 500 $m^2/g$ measured to DIN 66 131.

5. The process of claim 1, wherein a catalyst for the hydrogenating in (a) comprises ruthenium.

6. The process of claim 1, wherein an esterification in the reacting (b) is performed with at least one alcohol comprising 1 to 3 carbon atoms.

7. The process of claim 1, wherein an esterification in the reacting (b) is performed with at least one alcohol comprising 4 to 10 carbon atoms.

8. The process of claim 1, wherein an esterification in the reacting (b) is performed with methanol and, in the first distillation stage (c), a methyl carboxylate fraction essentially free of at least one 1,4-cyclohexanediol is obtained at a top of a column, and a bottom fraction comprising high boilers and the at least one 1,4-cyclohexanediol, and the methyl carboxylate fraction is transferred into the second distillation stage (d).

9. The process of claim 1, wherein an esterification in the reacting (b) is performed with n- or i-butanol and, in the first distillation stage (c), the at least one 1,4-cyclohexanediol is removed via a top with low boilers, and the at least one butyl carboxylate is obtained as a sidestream or as bottoms comprising them and are transferred into the second distillation stage (d).

10. The process of claim 1, wherein the distillation stages (c) and (d) are performed in a single column.

11. The process of claim 1, wherein a bottom product of the first distillation stage (c) is at least partly subjected to a further esterification with further addition of the low molecular weight alcohol and of an esterification catalyst and is separated in a separate distillation stage analogously to (b) and (c), or a further esterification is performed only after removal of the at least one 1,4-cyclohexanediol and the ester fraction comprising at least one carboxylic ester is introduced into the hydrogenating stage (e).

12. The process of claim 1, wherein an esterification in the reacting (b) is performed with methanol and, in the first distillation stage (c), a methyl carboxylate fraction essentially free of 1,4 cyclohexanediols is obtained at a top of a column, and a bottom fraction comprising high boilers and the at least one 1,4-cyclohexanediol, and the methyl carboxylate fraction is transferred into the second distillation stage (d).

13. The process of claim 2, wherein a catalyst for the hydrogenating in (a) comprises ruthenium.

14. The process of claim 3, wherein a catalyst for the hydrogenating in (a) comprises ruthenium.

15. The process of claim 4, wherein a catalyst for the hydrogenating in (a) comprises ruthenium.

16. The process of claim 1, wherein a catalyst for the hydrogenating in (a) comprises nickel.

17. The process of claim 1, wherein a catalyst for the hydrogenating in (a) comprises cobalt.

18. The process of claim 1, wherein a catalyst for the hydrogenating in (a) comprises rhenium.

19. The process of claim 1, wherein a catalyst for the hydrogenating in (a) comprises copper.

20. The process of claim 1, wherein an esterification in the reacting (b) is performed with at least one alcohol comprising 1 carbon atom.

* * * * *